(12) United States Patent
Carmona et al.

(10) Patent No.: US 10,947,055 B2
(45) Date of Patent: Mar. 16, 2021

(54) METHOD AND SYSTEM FOR LOCATING AN INSTRUMENTED OBJECT TRANSPORTED ALONG A PATH BY A CONVEYOR MACHINE

(71) Applicant: COMMISSARIAT A L'ENERGIE ATOMIQUE ET AUX ENERGIES ALTERNATIVES, Paris (FR)

(72) Inventors: Mikaël Carmona, Tencin (FR); Malvina Billeres, Grenoble (FR); Laure Peris y Saborit, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 15/533,467

(22) PCT Filed: Dec. 11, 2015

(86) PCT No.: PCT/EP2015/079381
§ 371 (c)(1),
(2) Date: Jun. 6, 2017

(87) PCT Pub. No.: WO2016/092064
PCT Pub. Date: Jun. 16, 2016

(65) Prior Publication Data
US 2017/0334657 A1    Nov. 23, 2017

(30) Foreign Application Priority Data
Dec. 12, 2014   (FR) ...................................... 14 62311

(51) Int. Cl.
*B65G 43/08* (2006.01)
*B65G 43/00* (2006.01)
(Continued)

(52) U.S. Cl.
CPC ............. *B65G 43/08* (2013.01); *B65G 43/00* (2013.01); *G01N 33/00* (2013.01); *G01V 11/002* (2013.01);
(Continued)

(58) Field of Classification Search
CPC .................... B65G 43/08; B65G 43/10; B65G 2203/0233; B65G 2203/0283; B65G 2203/043
See application file for complete search history.

(56) References Cited

U.S. PATENT DOCUMENTS

| 8,260,574 B1 | 9/2012 | Schuitema et al. |
| 2007/0114110 A1 | 5/2007 | Frost et al. |

(Continued)

OTHER PUBLICATIONS

International Search Report and Written Opinion dated Mar. 22, 2016 issued in corresponding application No. PCT/EP2015/079381; w/ English partial translation and partial machine translation (18 pages).

*Primary Examiner* — Matthew G Marini
(74) *Attorney, Agent, or Firm* — Westerman, Hattori, Daniels & Adrian, LLP (57) ABSTRACT

The object is provided with a system (1) for measuring at least one given physical quantity. The method comprises a step of measuring, by the measurement system (1), the time evolution of said physical quantity during the transportation of the object along the conveyance path, a step of recognising a plurality of indicia, each indicium corresponding to a path characteristic in the time evolution of the measured physical quantity, a step of determining a timeline of path characteristics corresponding to a sequence of recognised indicia, and a step of locating the object, which involves determining a match between the determined timeline of path characteristics and a predefined spatial representation relative to the conveyor machine.

21 Claims, 5 Drawing Sheets

(51) Int. Cl.
*G01N 33/00* (2006.01)
*G01V 11/00* (2006.01)

(52) U.S. Cl.
CPC ................ *B65G 2203/025* (2013.01); *B65G 2203/0233* (2013.01)

(56) References Cited

U.S. PATENT DOCUMENTS

| | | | |
|---|---|---|---|
| 2007/0152829 A1* | 7/2007 | Lindsay | G06K 19/0717 340/572.3 |
| 2010/0010664 A1 | 1/2010 | Kadaba | |
| 2010/0245105 A1 | 9/2010 | Smith | |
| 2011/0167721 A1* | 7/2011 | Lejeune | G05B 15/02 47/65 |
| 2011/0242299 A1 | 10/2011 | Kadaba | |
| 2012/0211330 A1* | 8/2012 | Ziegler | B65G 43/10 198/464.4 |
| 2013/0313072 A1* | 11/2013 | van de Loecht | B65G 54/02 198/464.1 |

* cited by examiner

METHOD AND SYSTEM FOR LOCATING AN INSTRUMENTED OBJECT TRANSPORTED ALONG A PATH BY A CONVEYOR MACHINE

The invention relates to a method and a system for locating an instrumented object transported along a path by a conveyor machine M, the object being provided with an instrument for measuring at least one given physical quantity.

A conveyor machine M for conveying objects, e.g. a parcel, a letter, a piece of waste or a product being manufactured, generally includes multiple successive modules intended to fulfill different functions and/or to execute different actions relative to the conveyed object.

The conveyor machine M may have a fault, which should be located. It may also be desirable to monitor the conveyance path of an object in order to check certain adjustment parameters of the machine. However, during its transportation by the conveyor machine M, in an at least partially confined environment, it is difficult to have access to the object. As a result, it is also difficult to locate the object during its transportation by the conveyor machine M.

The present invention will improve the situation.

For this purpose, the invention relates to a method for locating an instrumented object transported along a path by a conveyor machine, said object being provided with a measurement system for measuring at least one given physical quantity, including a step of measuring, by the measurement system, the time evolution of said physical quantity during the transportation of the object along the conveyance path, a step of recognizing a plurality of indicia, each indicium corresponding to a path characteristic in the time evolution of the measured physical quantity, a step of determining a timeline of path characteristics corresponding to a sequence of recognized indicia and a step of locating the object during which a correspondence is determined between the determined timeline of path characteristics and a predetermined spatial representation relating to the conveyor machine.

According to the invention, the measurements of physical quantities performed by the instrumented object make it possible to identify the particular characteristics of the path of the object. Indeed, certain particular path characteristics leave indicia, or signatures, distinguishable in the time evolution of one or more measured physical quantities. The object may be located from one or more path characteristics identified with the aid of one or more recognized indicia. Location may consist in determining where the object is located along a conveyance path at a given instant or, in the case of a conveyor machine having multiple possible paths, in determining the path taken by the object.

Advantageously, the time evolution is measured of at least one of the physical quantities of the group comprising an acceleration, a distance, an inclination, a magnetic field, an angular position, a temperature, a sound, and a pressure.

Also advantageously, the sequence of recognized indicia includes different types of indicia, notably indicia of the group comprising an acceleration, a distance, an inclination, a magnetic field, an angular position, a temperature, a sound, and a pressure.

In one particular embodiment, during the step of recognizing, at least one of the indicia is recognized of the group comprising a measured magnetic field strength peak corresponding to an electric motor, a measured distance peak corresponding to a transition from one module to another module of the conveyor machine and a measured acceleration plateau corresponding to a turn.

The time evolutions of a plurality of physical quantities may be measured.

Advantageously, the step of recognizing is performed with the aid of a data table containing, for each characteristic of a set of predefined path characteristics, characterization data of the indicium corresponding to said path characteristic.

In a particular embodiment, the conveyor machine comprising a plurality of possible conveyance paths, during the step of locating, the path taken by the instrumented object is determined, from among the plurality of possible conveyance paths, from the determined timeline of path characteristics.

The method may include a step of monitoring the correct operation of the conveyor machine from the determined timeline of path characteristics. A conceivable application of the locating method of the invention is to monitor the operation of the conveyor machine.

The method may also include a step of detecting a fault in the conveyance path of the object, based on an analysis of the time evolution of a particular measured physical quantity.

Advantageously, it includes a step of transmitting data on the evolution of the measured physical quantity to an external analysis device and the steps of recognizing at least one indicium and of locating the object are executed by the external analysis device.

The invention also relates to a system for locating an object transported along a path by a conveyor machine, characterized in that it includes an instrumented object provided with a measurement system for measuring at least one given physical quantity, arranged for measuring the time evolution of said physical quantity during the transportation of the object along the conveyance path, and an external analysis device comprising a recognition module suitable for recognizing a plurality of indicia, each indicium corresponding to a path characteristic in the time evolution of the measured physical quantity, a module for determining a timeline of path characteristics corresponding to a sequence of recognized indicia and a locating module for locating the object suitable for establishing a correspondence between the determined timeline of path characteristics and a predetermined spatial representation relating to the conveyor machine stored in memory.

The system advantageously includes all or part of the following features:
- the external analysis device includes a memory for storing a data table containing, for each characteristic of a set of predefined path characteristics, characterization data of an indicium corresponding to said path characteristic;
- the external analysis device includes a monitoring module for monitoring the correct operation of the conveyor machine from the determined timeline of path characteristics;
- it includes a fault detecting module, arranged for detecting a fault in the conveyance path of the object, via analysis of the time evolution of a particular measured physical quantity.

The invention also relates to an analysis device intended to locate an instrumented object transported along a path by a conveyor machine, said instrumented object being provided with a measurement system for measuring at least one given physical quantity, arranged for measuring the time evolution of said physical quantity during the transportation of the object along the conveyance path, said analysis device including a communication interface for communicating with the measurement system intended to receive measured data relating to the time evolution of said physical quantity during the transportation of the object along the conveyance path, a recognition module suitable for recognizing a plurality of indicia, each indicium corresponding to a path characteristic in the time evolution of the measured physical quantity, a module for determining a timeline of path characteristics corresponding to a sequence of recognized indicia and a locating module for locating the object suitable for establishing a correspondence between the determined timeline of path characteristics and a predetermined spatial representation relating to the conveyor machine stored in memory.

The invention will be better understood with the aid of the following description of a particular embodiment of the method for locating an instrumented object transported by a conveyor machine M, with reference to the accompanying drawings in which.

With respect to FIGS. 6A and 6C.

The invention relates to a method for locating an instrumented object transported along a path by a conveyor machine M.

The conveyor machine M is intended to transport objects along a conveyance path. Such a conveyor machine M may be used on a production line in many fields (automotive, pharmaceutical, agri-foodstuffs, cardboard manufacture, etc.) or within a system for sorting objects such as parcels, mail or waste. The conveyance path may pass through different modules intended to perform different respective actions on the object (e.g. weighing a parcel, reading a bar code on the parcel, etc.). It may include straight portions, turns, gradients, etc. The path may also pass near particular devices, notably motors.

"Instrumented object" is understood to designate an object capable of being transported by the conveyor machine M and provided with a measurement instrument or system. The object is, for example, a parcel, in the case of a conveyor machine M for a parcel sorting system, or a motor vehicle structure in the case of a conveyor machine M for an automobile production line.

The measurement instrument or system is intended to measure one or more physical quantities. It includes one or more measurement sensors. The measured quantity or quantities may include, non-exhaustively: an acceleration, a distance, an inclination, a magnetic field, an angular position, a temperature, a sound, a light intensity measurement (diodes) and a pressure. The acceleration may be a 3D acceleration. It is measured by a triaxial accelerometer. The distance may, for example, be a distance with respect to an internal wall of a module or with respect to a lower surface (bottom of a module or floor). It may be measured by a distance sensor provided with a transmitter and a receiver of light signals, suitable for measuring the round-trip time of a light signal transmitted by the transmitter, reflected on the internal wall of the module and received by the receiver. The inclination may be an angle of inclination with respect to the horizontal. It may be measured by an inclinometer. The magnetic field may be measured by a magnetometer. The angular position may be measured by a gyroscope. The temperature, sound and pressure may be measured by a thermal sensor, an acoustic sensor and a pressure sensor, respectively.

Figure 2:
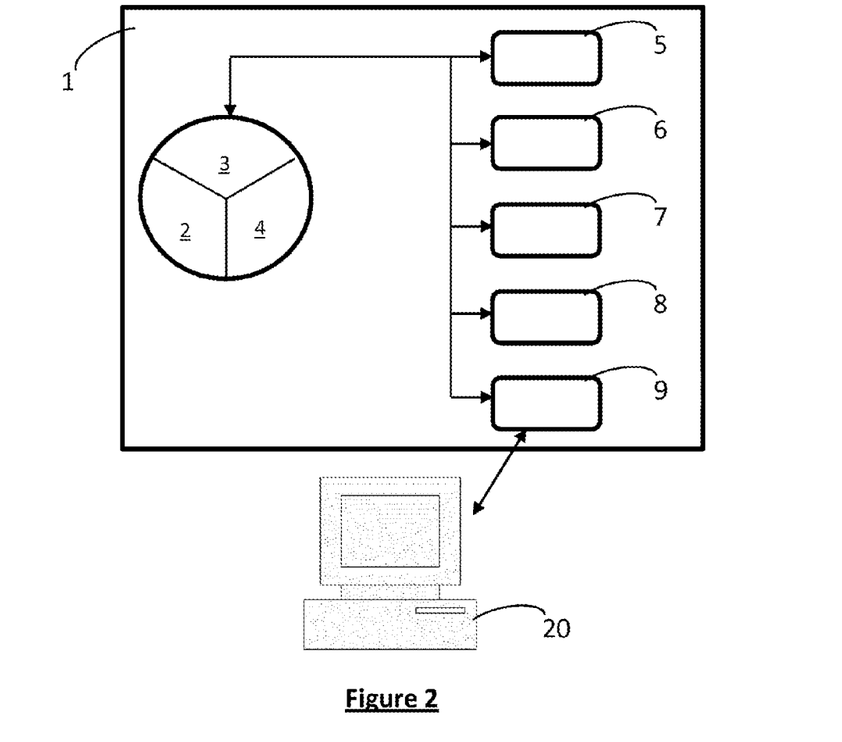
FIG. 2 represents a functional block diagram of a measurement instrument carried by an object.

FIG. 2 represents a functional block diagram of a measurement system 1, according to a particular embodiment. The measurement system 1 includes multiple sensors 2-4, a power supply battery 5, a recording memory 6, a microcontroller 7, a user interface 8 and a communication interface 9 for communicating with an external analysis device 20.

In the particular example described here, the sensors include a component 2 combining a triaxial accelerometer and a triaxial magnetometer, an optical distance sensor 3 and a gyrometer sensor 4. The distance sensor 3 includes an element for transmitting an optical signal, an element for receiving the transmitted optical signal, after its reflection on a surface, an element for calculating the round-trip time of the signal (i.e. the duration between the instant of transmission and the instant of reception of the signal, the latter having been reflected by a surface) and an element for determining the distance between the sensor 3 and the reflection surface.

The communication interface 9 here includes a mini-USB connector intended to be physically connected to the external analysis device 20. As a variant, it could include a radio communication interface intended to communicate by radio with a corresponding radio communication interface of the analysis device 20.

The user interface 8 here includes:
an ON/OFF button for switching the measurement system 1 on or off,
a START/STOP button for starting or stopping an acquisition of measurement data and
two LEDs, one green, intended to report a correct operation, and the other red intended to report either a fault (continuous red signal), or a discharge of the battery (flashing red signal).

The sensors 2-4, the battery 5, the memory 6 and the interfaces 8 and 9 are connected to the microcontroller 7 which is intended to monitor the operation of these elements. The microcontroller 7 is also connected to a "reset" (i.e. reinitialization) button for the microcontroller 7.

All the measurement system elements, with the exception of the distance sensor 3, are mounted on a main printed circuit board. The distance sensor elements 3 are connected to a secondary printed circuit board, smaller in size than the main board. The secondary board is housed in a slot arranged in one edge (front or rear in the direction of movement of the measurement system) of the main board. It extends in a plane perpendicular to that of the main board.

The battery may be a button cell mounted on the main board. Alternatively, it may be connected to connectors, provided on the main board, by a cable.

The measurement system or instrument 1 has technical characteristics, notably dimensions (height, width, thickness), a weight, an autonomy and a memory capacity, which are suited to the envisaged application. The autonomy must in particular be sufficient to make it possible to take a measurement throughout the whole conveyance path.

Figure 4:
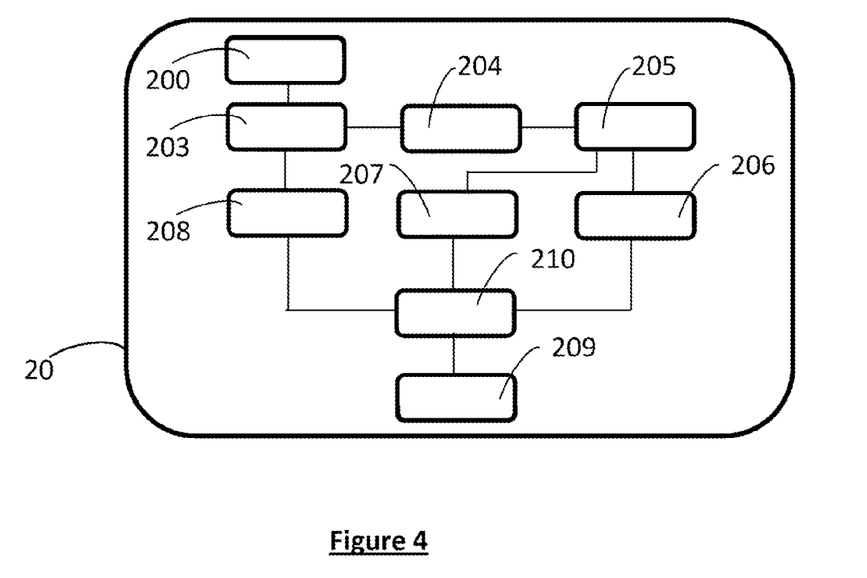
FIG. 4 represents a functional block diagram of an external analysis device.

The analysis device 20 includes:

a communication interface 200 for communicating with the measurement system 1;

a memory 201 containing a correspondence table T;

a memory 202 containing data relating to a predetermined spatial representation relating to the conveyor machine M;

a memory 203 for storing data relating to the time evolution of one or more physical quantities measured by the measurement system 1 carried by an object transported by the conveyor machine M then transmitted to the device 20;

a recognition module 204 for recognizing indicia corresponding to conveyance path characteristics;

a module 205 for determining a timeline of path characteristics corresponding to recognized indicia;

a locating module 206;

an operation monitoring module 207 intended to monitor the correct operation of the conveyor machine M;

a fault detecting module 208;

a user interface 209.

All the elements 200-209 of the analysis device are connected to a central control unit 210, in this instance a microprocessor, intended to monitor the operation of these elements. The roles of these different elements will appear in the following description of the method. The analysis device 20 is termed "external" because it is located outside the conveyance path or paths of the conveyor machine M. Here it refers to a computer device separate from the conveyor machine M. The device 20 also includes a configuration module, not represented, intended to configure the analysis device 20, notably to record the table T and the spatial representation of the conveyor machine M in the memories 201 and 202.

The configuration module (not represented) and the modules 204 to 208 are software modules comprising software instructions intended to control the execution of the corresponding method steps explained later, when the software module is executed by the central control unit 210.

The data table T, recorded in the memory 201, contains, for each characteristic of a set of predefined path characteristics, characterization information or data of an indicium (or signature) corresponding to the path characteristic considered. A path characteristic, such as a turn or a motor located nearby, leaves an "indicium", or "signature," which is specific thereto, in the time evolution of one or more appropriate physical quantities. For example, a motor placed near the path induces a peak strength in the time evolution of the strength of the magnetic field measured when the instrumented object passes near the motor. Examples of path characteristics and corresponding indicia are given below:

TABLE T

| Path characteristic | Indicium |
|---|---|
| Motor nearby | Magnetic field strength peak |
| Turn | Acceleration plateau |
| Change of module | Distance peak (corresponds to a space between two modules that are not perfectly adjacent) |
| Start of conveyance | Transition between a distance plateau then a non-stationary distance phase |
| End of conveyance | Transition between a non-stationary distance phase then a distance plateau |

The indicium may be known precisely a priori from information relating to the design of the conveyor machine (e.g. the indicium of a gradient in the path, the gradient having a certain fixed inclination). As a variant, the indicium may be determined during a preliminary conveyance.

FIGS. 5, 6A-6B and 7, represent the time evolutions of different physical quantities (distance, triaxial acceleration and electric motor current), measured by the measurement system for measuring the object $OB_1$ transported by a conveyor machine, by way of purely illustrative examples only intended for better understanding the data table T.

Figure 5:
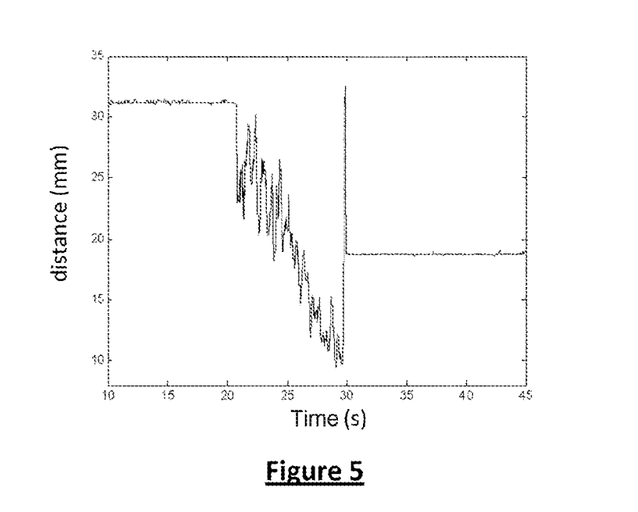
FIG. 5 represents the time evolution of a measured distance during the transport of an instrumented object by the conveyor machine M.

FIG. 5 represents the time evolution of a distance measured by a distance sensor along a conveyance path. The curve represented includes three phases: a first stationary phase (or plateau) between 10 s and 20 s, a second non-stationary intermediate phase, which descends overall, between 20 s and 30 s and a third stationary phase (or plateau) beyond 30 s. The first transition at 20 s between the first plateau and the non-stationary intermediate phase constitutes the indicium of the "start of conveyance" path characteristic. The second transition at 30 s between the non-stationary intermediate phase and the second plateau is the indicium of the "end of conveyance" path characteristic.

Figure 6A:
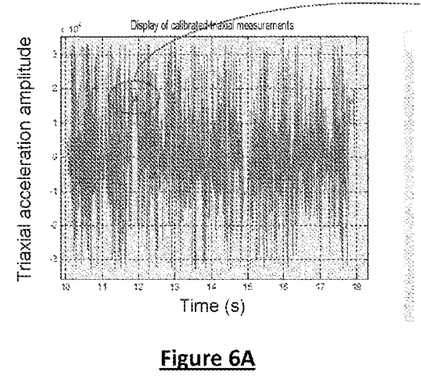
FIG. 6A represents the time evolution of a measured acceleration during the transportation of an instrumented object by the conveyor machine M along a path that is partially represented in FIG. 6C.
Figure 6B:
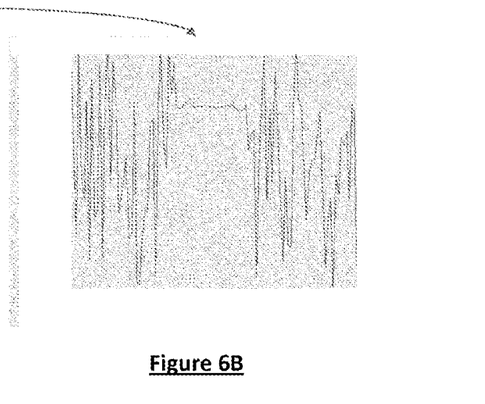
FIG. 6B represents a zoom-in of a part of the time evolution of acceleration in FIG. 6A.
Figure 6C:
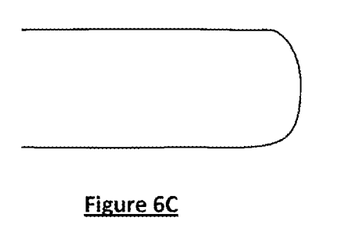

FIG. 6A represents the time evolution of a triaxial acceleration measured by a sensor along a conveyance path as partially represented in FIG. 6C. This path comprises a 180° turn. FIG. 6B represents a zoom-in on this acceleration curve between the instants 11.4 s and 12 s. In the zoom-in of FIG. 6C, a stationary acceleration phase, i.e. a plateau, around the instant 11.7 s may be observed. This acceleration plateau constitutes the indicium of a turn in the conveyance path.

Figure 7:
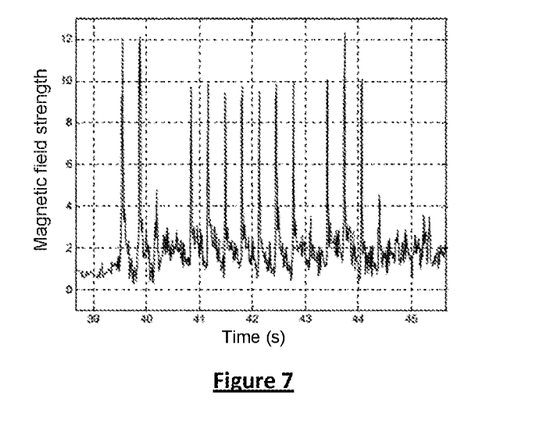
FIG. 7 represents the time evolution of a measured magnetic field during the transportation of an instrumented object by the conveyor machine M.
Figure 8:
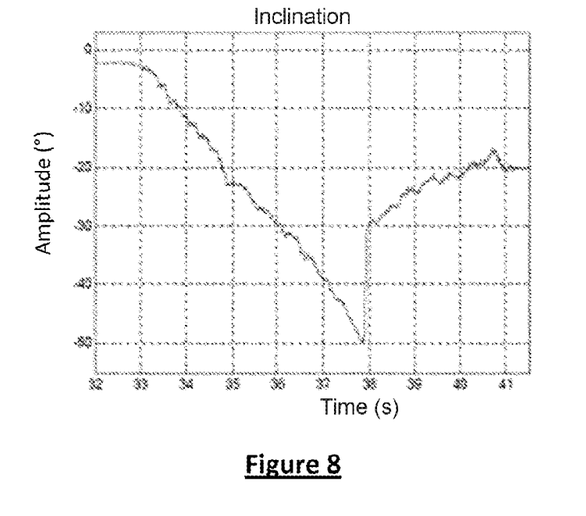
FIG. 8 represents the time evolution of a measured inclination during the transportation of an instrumented object by the conveyor machine M.

FIG. 7 represents the time evolution of a magnetic field strength measured by a sensor along a conveyance path passing near twelve motors. Twelve magnetic field strength peaks greater than 6 gauss may be observed on this curve. These magnetic field peaks constitute the indicia of motors located near the conveyance path.

Table T is created and recorded in the memory 201 of the analysis device 20 during a step E0 of configuration of the analysis device. This configuration E0 may be executed during a coupling of the analysis device 20 with the conveyor machine M.

The memory 202 contains data relating to a predetermined spatial representation relating to the conveyor machine M. This spatial representation includes spatial data relating to the machine, notably to the conveyance path or to the plurality of conveyance paths that it contains. These spatial data may be represented in the form of a map or plan of the conveyor machine M. This map or this plan depicts the characteristics of the conveyance path or paths: straight parts, turns, motors, etc. The data relating to the spatial representation of the conveyor machine M are recorded in the memory 202 during the configuration E0 of the analysis device and the coupling thereof to the conveyor machine M.

Figure 3:
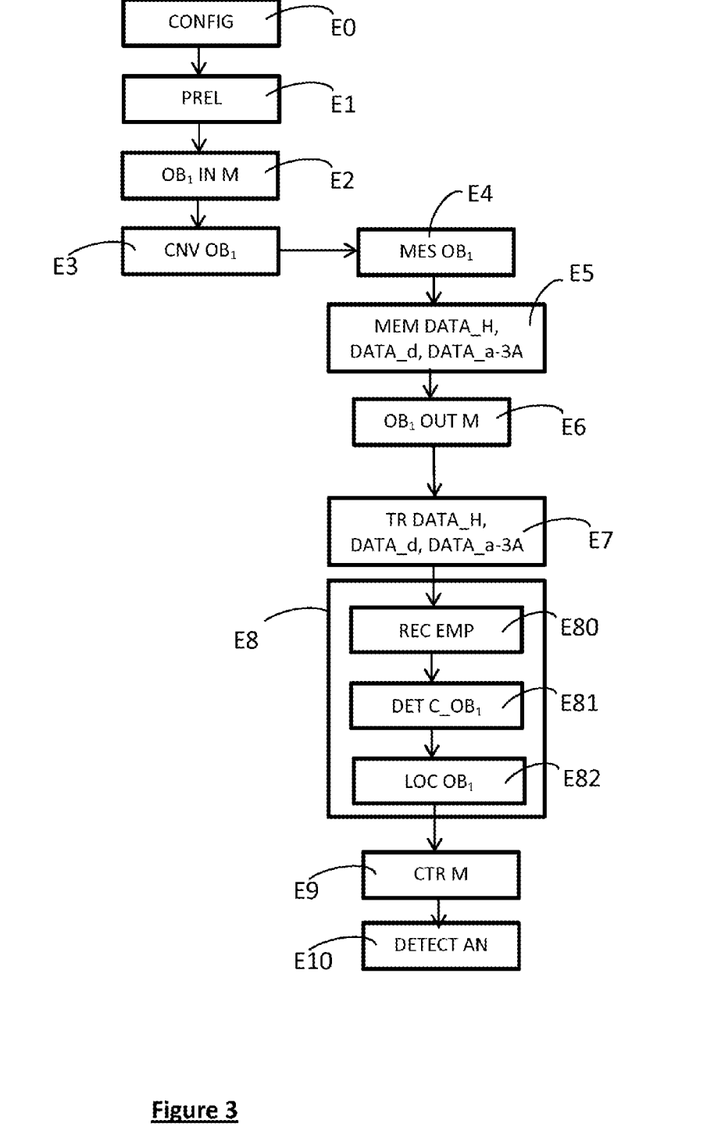
FIG. 3 represents a flowchart of the steps of the locating method according to a particular embodiment of the invention.

A particular embodiment of the method for locating an instrumented object transported along a path by a conveyor machine M will now be described with reference to FIG. 3.

During a preliminary step E1, the measurement system or instrument 1 is placed on a control object $OB_0$ and fastened thereto with double-sided Scotch tape or with any other suitable fastening means. The control object $OB_0$ corresponds to an object capable of being conveyed by the conveyor machine M. This is, for example, a parcel, in the case of a parcel sorting application, a letter, in the case of a mail sorting application, a piece of waste, or a motor vehicle structure in the case of an automobile production or assembly line application.

The control object thus instrumented, denoted by $OB_1$, is then inserted in the conveyor machine M, at the entrance thereof, during a step E2.

The method then includes a step of conveyance E3, during which the instrumented control object is transported by the conveyor machine M along a conveyance path PC.

The conveyance path PC includes multiple successive sections corresponding, for example, to different modules intended to perform different actions relating to the object. Each portion has specific characteristics. For example, a portion may:

be linear or comprise one or more turn(s);
be inclined or horizontal;
comprise one or more motors.

Figure 1:
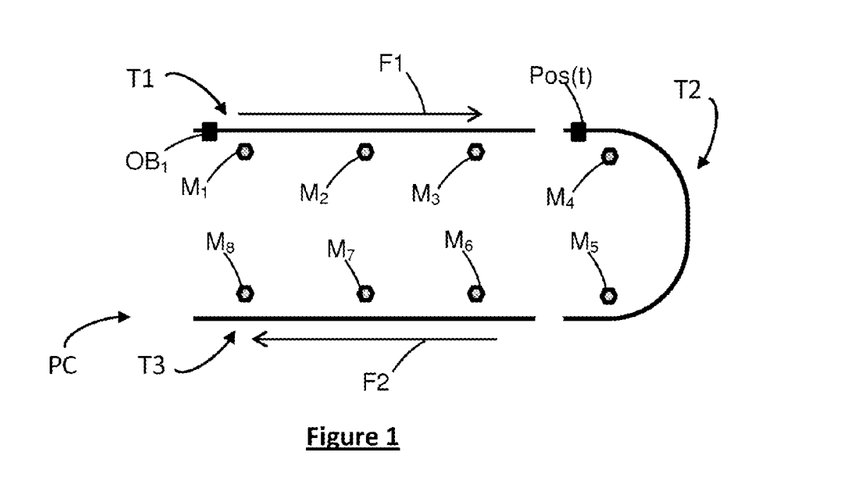
FIG. 1 represents, as an illustrative example, a portion of a conveyance path along which an instrumented object is intended to be transported.

By way of an illustrative example, FIG. 1 represents a portion of a conveyance path comprising three sections T1, T2 and T3. Each section of the conveyance path corresponds to a path module. The three sections T1, T2 and T3 are horizontal. The arrows F1 and F2 represent the direction of movement of an object along the path. The first section T1 is linear, horizontal and passes near three successive motors $M_1$, $M_2$, $M_3$. The second section T2 comprises two turns and passes near two motors $M_4$, located just before the first turn, $M_5$, located just after the second turn, in the direction of movement of the object. The third section T3 is linear and passes near three successive motors $M_6$, $M_7$, $M_5$.

In parallel with step of conveyance E3, the method includes a step E4 of measuring the time evolution of at least one physical quantity during the transportation of the object along the conveyance path PC. This step of measuring E4 is executed by the measurement system 1 carried by the object $OB_1$. In the particular example described here, the system 1 measures:

a magnetic field H with the aid of the accelero-magnetometer sensor 2,
a distance d with the aid of the optical distance sensor 3,
a triaxial acceleration a-3A with the aid of the accelero-magnetometer sensor 2.

The magnetic field (DATA_H), distance (DATA_d) and acceleration (DATA_a-3A) measured data, are recorded in the memory 6 of the measurement system 1, during a step E5.

At the end of the transportation of the object $OB_1$ by the conveyor machine M, the object $OB_1$ exits from the conveyor machine M, during a step E6. The measurement system 1 is separated from the control object $OB_0$. Then, during a step E7, the recorded measurement data (DATA_H, DATA_d, DATA_a-3A) are transmitted to the analysis device 20, here after physical connection of the system 1 to the analysis device 20. The measurement data transmitted by the system 1 are received via the communication interface 200 and recorded in the memory 203 of the analysis device 20.

The method then passes on to an analysis operation E8 for analyzing the recorded measurement data.

The analysis operation includes a step E80 of recognizing or identifying indicia in the time evolution of the different measured physical quantities. This step E80 is implemented by the recognition module 204 for recognizing indicia. As previously explained, an indicium corresponds to a path characteristic.

The step of recognizing indicia E80 is performed with the aid of the data table T recorded in the memory 201 of the analysis device 20. The data table T could, alternatively, be accessible by the device 20 through a network such as the Internet.

During the step of recognizing E80, the analysis device 20 may recognize at least one of the indicia of the group comprising:

a magnetic field strength peak corresponding to an electric motor,
a distance peak corresponding to a transition from one module to another module of the conveyor machine M and
an acceleration plateau corresponding to a turn.

The method then includes a step E81 of determining a timeline $C\_OB_1$ of path characteristics corresponding to successive recognized indicia. This timeline $C\_OB_1$ definitively corresponds to the path characteristics as perceived by the instrumented object $OB_1$. Step E81 is implemented by the module 205 of the analysis device.

The example will be taken of the portion of conveyance path in FIG. 1. During the step of recognizing E80, the analysis device 20 successively recognizes:

three successive magnetic field strength peaks;
a distance peak;
a magnetic field strength peak;
an acceleration plateau;
a magnetic field strength peak;
a distance peak;
three successive magnetic field strength peaks.

During step E81, the analysis device 20 determines the following timeline $C\_OB_1$ of path characteristics, from the successive recognized indicia:

three successive motors near the path;
a change of module;
a motor near the path;
a turn;
a motor near the path;
a change of module;
three successive motors near the path.

In the determined timeline $C\_OB_1$, each characteristic of the sequence of determined path characteristics may be associated with time data corresponding to the instant at which the object $OB_1$ has perceived or detected the considered path characteristic or to the time window during which the object $OB_1$ has perceived or detected the considered path characteristic. However, the timeline $C\_OB_1$ may only contain a sequence (i.e. an ordered series) of path characteristics.

The method then includes a step E82 of locating the instrumented object $OB_1$. This step E82 is implemented by the locating module 206 of the analysis device 20. During this step of locating E82, a correspondence is established between the determined timeline $C\_OB_1$ and the predetermined spatial representation RS relating to the conveyor machine M. This correspondence makes it possible to determine the position of the object $OB_1$ in the conveyor machine M and more particularly along its conveyance path, at each instant of the conveyance of the object $OB_1$.

The conveyor machine M may include multiple possible conveyance paths. In this case, the step of locating E82 makes it possible to determine, from among the set of possible paths, the path taken by the object $OB_1$.

It is assumed, for example, that it is intended to locate the object $OB_1$ in the conveyor machine M, and more precisely along the conveyance path part represented in FIG. 1, at a given instant t, knowing that, at this instant t, the object $OB_1$ is located at the start of the section T2 at the position Pos(t) as represented in FIG. 1. The timeline C_$OB_1$ is determined for this purpose. This timeline may only be partially determined. For example, only the part of the timeline between the start of the conveyance and the instant t may be determined. The timeline C_$OB_1$ includes, between a conveyance starting instant and the instant t, the following path characteristics: three successive motors near the path, followed by a change of module. During the step of locating E82, a correspondence is determined between the determined timeline C_$OB_1$ (or the determined timeline part) and the predetermined spatial representation relating to the conveyor machine M. It is deduced that, at instant t, the object $OB_1$ is located at the start of the section T2 on the spatial representation.

The method may then include a step E9 of monitoring the correct operation of the conveyor machine M. This step E9 is implemented by the monitoring module 207 of the analysis device. The operation of the conveyor machine M may be monitored from the determined path characteristics timeline C_$OB_1$. It may consist in checking whether the object $OB_1$ is taking the correct path, from among a set of possible paths. It may also consist in checking whether the conveyance speed of the object $OB_1$ along its conveyance path, or a part of this path, complies with a desired speed. It may further consist in checking that the object $OB_1$ is correctly following the conveyance path, i.e. that it complies with certain predefined conveyance conditions or parameters.

The method may also include a step E10 of detecting a fault in the conveyance path of the object $OB_1$. This step of detecting E10 is implemented by the detecting module 208 of the analysis device. Fault detection may be based on an analysis of the time evolution of a particular physical quantity measured by the measurement system 1 during the transportation of the object $OB_1$ along the conveyance path. For example, this may involve the inclination, notably the inclination of an arbitrary vector, fixed and attached to the conveyed object, with respect to the plane orthogonal to the direction of the Earth's gravity field (or horizontal plane) of the object, defined, for example, with respect to a horizontal plane. FIG. 7 represents the time evolution of an inclination measured by the object $OB_1$ during its conveyance, by way of a purely illustrative example. A break may be observed in the time evolution of the inclination around the instant 38 s. This break corresponds, for example, to an impact of the object $OB_1$ with an incorrectly positioned part. The shutdown of a motor may also be detected during step E9, by detection of the absence of the corresponding magnetic field strength peak.

The invention claimed is:

1. A method for locating an instrumented object transported along a path by a conveyor machine, the object being provided with a measurement system for measuring at least one given physical quantity, the method comprising:

measuring, by the measurement system having a sensor on the object, a time evolution of the physical quantity during the transportation of the object along the conveyance path, during the transportation of the object along the conveyance path, recognizing a plurality of indicia, each indicium corresponding to a path characteristic in the time evolution of the measured physical quantity measured by the measurement system during the transportation of the object along the conveyance path, during the transportation of the object along the conveyance path, determining a timeline of path characteristics corresponding to a sequence of recognized indicia based on said recognizing of the plurality of indicia, and during the transportation of the object along the conveyance path, locating the object based on a correspondence between the determined timeline of path characteristics and a predetermined spatial representation relating to the conveyor machine, wherein the physical quantity is selected from the group consisting of a magnetic field, a temperature, a sound, and a pressure.

2. The method as claimed in claim 1, wherein the measurement system is configured for measuring at least one additional physical quantity selected from the group consisting of an acceleration, a distance, an inclination, and an angular position.

3. The method as claimed in claim 2, wherein the sequence of recognized indicia includes indicia selected from the group consisting of an acceleration, a distance, an inclination, a magnetic field, an angular position, a temperature, a sound, and a pressure.

4. The method as claimed in claim 1, wherein the measurement system of the object includes a magnetic field sensor measuring a magnetic field corresponding to the presence of an electric motor along the path, and wherein, during the recognizing, a measured magnetic field strength peak corresponding to a proximity of the object to an electric motor along the path is recognized.

5. The method as claimed in claim 1, wherein the measuring includes measuring the time evolutions of a plurality of physical quantities.

6. The method as claimed in claim 1, wherein the recognizing is performed with the aid of a data table containing, for each characteristic of a set of predefined path characteristics, characterization data of the indicium corresponding to the path characteristic.

7. The method as claimed in claim 1, wherein the conveyor machine comprises a plurality of possible conveyance paths, and during the locating, the path taken by the instrumented object is determined, from among the plurality of possible conveyance paths, from the determined timeline of path characteristics.

8. The method as claimed in claim 1, comprising monitoring the correct operation of the conveyor machine from the determined timeline of path characteristics.

9. The method as claimed in claim 8, comprising detecting a fault in the conveyance path of the object, based on an analysis of the time evolution of a particular measured physical quantity.

10. The method as claimed in claim 1, comprising transmitting data on the evolution of the measured physical quantity to an external analysis device, the recognizing at least one indicium and the locating of the object being executed by the external analysis device.

11. A system for locating an object transported along a path by a conveyor machine, comprising:
- an instrumented object provided with a measurement system configured to measure at least one given physical quantity during the transportation of the object along the conveyance path, and configured to measure the time evolution of the physical quantity measured by the measurement system having a sensor on the object during the transportation of the object along the conveyance path, and
- an external analysis device comprising
  - a recognition module configured to recognize a plurality of indicia during the transportation of the object along the conveyance path, each indicium corresponding to a path characteristic in the time evolution of the measured physical quantity measured by the measurement system,
  - a module configured to determine during the transportation of the object along the conveyance path a timeline of path characteristics corresponding to a sequence of recognized indicia based on the recognizing of the plurality of indicia by the recognition module, and
  - a locating module configured to locate the object during the transportation of the object along the conveyance path based on a correspondence between the determined timeline of path characteristics and a predetermined spatial representation relating to the conveyor machine stored in memory,
- wherein the physical quantity is selected from the group consisting of a magnetic field, a temperature, a sound, and a pressure.

12. The system as claimed in claim 11, wherein the external analysis device includes a memory for storing a data table containing, for each characteristic of a set of predefined path characteristics, characterization data of an indicium corresponding to the path characteristic.

13. The system as claimed in claim 12, wherein the external analysis device includes a monitoring module for monitoring the correct operation of the conveyor machine from the determined timeline of path characteristics.

14. The system as claimed in claim 13, comprising a fault detecting module, arranged for detecting a fault in the conveyance path of the object, via analysis of the time evolution of a particular measured physical quantity.

15. The system as claimed in claim 12, comprising a fault detecting module, arranged for detecting a fault in the conveyance path of the object, via analysis of the time evolution of a particular measured physical quantity.

16. The system as claimed in claim 11, wherein the external analysis device includes a monitoring module for monitoring the correct operation of the conveyor machine from the determined timeline of path characteristics.

17. The system as claimed in claim 16, comprising a fault detecting module, arranged for detecting a fault in the conveyance path of the object, via analysis of the time evolution of a particular measured physical quantity.

18. The system as claimed in claim 11, comprising a fault detecting module, arranged for detecting a fault in the conveyance path of the object, via analysis of the time evolution of a particular measured physical quantity.

19. The system as claimed in claim 11, wherein the measurement system of the object includes a magnetic field sensor measuring a magnetic field corresponding to the presence of an electric motor along the path, and wherein, during the recognizing, a measured magnetic field strength peak corresponding to a proximity of the object to an electric motor along the path is recognized.

20. An analysis device intended to locate an instrumented object transported along a path by a conveyor machine, the instrumented object being provided with a measurement system for measuring at least one given physical quantity, arranged for measuring the time evolution of the physical quantity during the transportation of the object along the conveyance path, the analysis device comprising:
- a communication interface configured to communicate, during transportation of the object along the conveyance path, with the measurement system having a sensor on the object and to receive from the measurement system measured data relating to the time evolution of the physical quantity during the transportation of the object along the conveyance path,
- a recognition module configured to recognize a plurality of indicia during transportation of the object along the conveyance path, each indicium corresponding to a path characteristic in the time evolution of the measured physical quantity received from the measurement system during transportation of the object along the conveyance path,
- a module configured to determine during transportation of the object along the conveyance path a timeline of path characteristics corresponding to a sequence of recognized indicia based on the recognizing of the plurality of indicia by the recognition module, and
- a locating module configured to locate the object during the transportation of the object along the conveyance path based on a correspondence between the determined timeline of path characteristics and a predetermined spatial representation relating to the conveyor machine stored in memory,
- wherein the physical quantity is selected from the group consisting of a magnetic field, a temperature, a sound, and a pressure.

21. The analysis device as claimed in claim 20, wherein the measurement system of the object includes a magnetic field sensor measuring a magnetic field corresponding to the presence of an electric motor along the path, and wherein, during the recognizing, a measured magnetic field strength peak corresponding to a proximity of the object to an electric motor along the path is recognized.

\* \* \* \* \*